(12) United States Patent
Dietmaier (10) Patent No.: US 6,664,064 B1
(45) Date of Patent: Dec. 16, 2003

(54) METHOD FOR MELTING CURVE ANALYSIS OF REPETITIVE PCR PRODUCTS

(75) Inventor: Wolfgang Dietmaier, Regensburg (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 25 days.

(21) Appl. No.: 10/003,998

(22) Filed: Nov. 14, 2001

(30) Foreign Application Priority Data

Nov. 15, 2000 (EP) .............................................. 00124897

(51) Int. Cl.⁷ ................................................. C12Q 1/68
(52) U.S. Cl. .......................... 435/6; 536/23.1; 536/24.3
(58) Field of Search ............................. 435/6; 536/23.1, 536/24.3; 935/76, 77, 78

(56) References Cited

U.S. PATENT DOCUMENTS

| | | | |
|---|---|---|---|
| 5,075,217 A | * | 12/1991 | Weber |
| 5,582,979 A | * | 12/1996 | Weber |
| 6,083,701 A | * | 7/2000 | Reeve |
| 6,140,054 A | * | 10/2000 | Wittwer et al. |
| 6,218,119 B1 | * | 4/2001 | Kuiper et al. |
| 6,238,866 B1 | * | 5/2001 | Yeh et al. |

FOREIGN PATENT DOCUMENTS

| | | | |
|---|---|---|---|
| EP | 1207210 A1 | * | 5/2002 |
| JP | 2003093075 | * | 4/2003 |
| WO | WO9727328 A1 | * | 7/1997 |
| WO | WO9811433 A1 | * | 3/1998 |
| WO | WO9818965 A1 | * | 5/1998 |
| WO | WO9912031 A1 | * | 3/1999 |

OTHER PUBLICATIONS

Weber et al., Am. J. of Human Genetics 44 : 388–396 (1989).*

Litt et al., Am. J. of Human Genetics 44 : 397–401 (1989).*

* cited by examiner

Primary Examiner—Ethan Whisenant
(74) Attorney, Agent, or Firm—Pennie & Edmonds LLP

(57) ABSTRACT

The invention relates to method, wherein the number of repeat sequences which are present in a sample is detemined by means of melting temperature analysis. More precisely, the invention relates to a method for analysis of a target nucleic acid consisting of repetitive and non repetitive sequences comprising (i) hybridization of at least one polynucleotide hybridization probe comprising a first segment which is complementary to a non repetitive region and a second segment which is compementary to an adjacent repetitive region, said second segment consisting of a defined number of repeats and (ii) determination of the melting point temperature of the hybrid which has been formed between the target nucleic acid and the at least one hybridization probe.

7 Claims, 5 Drawing Sheets

target nucleic acid

B)

target nucleic acid

Fig. 2

Fig. 3    BAT 26

A)

Normal tissue
Blood
H₂O

B)

MSI-H Tumor
Blood
H₂O

Fig. 4    BAT25

A)

Normal tissue
Blood
$H_2O$

Tm = 44.83

B)

MSI-H Tumor
Blood
$H_2O$

Tm = 42.32    Tm = 44.83

Fig. 5    Duplex-PCR

A)

B)

SEQUENCE LISTING

<160> NUMBER OF SEQ ID NOS: 8

<210> SEQ ID NO 1
<211> LENGTH: 21
<212> TYPE: DNA
<213> ORGANISM: Homo sapiens

```
<400> SEQUENCE: 1
tgactacttt tgacttcagc c                                              21

<210> SEQ ID NO 2
<211> LENGTH: 21
<212> TYPE: DNA
<213> ORGANISM: Homo sapiens

<400> SEQUENCE: 2
aaccattcaa catttttaac c                                              21

<210> SEQ ID NO 3
<211> LENGTH: 23
<212> TYPE: DNA
<213> ORGANISM: Homo sapiens

<400> SEQUENCE: 3
gcagcagtca gagcccttaa cct                                            23

<210> SEQ ID NO 4
<211> LENGTH: 32
<212> TYPE: DNA
<213> ORGANISM: Homo sapiens

<400> SEQUENCE: 4
tcaggtaaaa aaaaaaaaaa aaaaaaaaaaaa                                   32

<210> SEQ ID NO 5
<211> LENGTH: 20
<212> TYPE: DNA
<213> ORGANISM: Homo sapiens

<400> SEQUENCE: 5
tcgcctccaa gaatgtaagt                                                20

<210> SEQ ID NO 6
<211> LENGTH: 21
<212> TYPE: DNA
<213> ORGANISM: Homo sapiens

<400> SEQUENCE: 6
tctgcatttt aactatggct c                                              21

<210> SEQ ID NO 7
<211> LENGTH: 29
<212> TYPE: DNA
<213> ORGANISM: Homo sapiens

<400> SEQUENCE: 7
caaaaaaaaa aaaaaaaaaa aaaaaatca                                      29

<210> SEQ ID NO 8
<211> LENGTH: 28
<212> TYPE: DNA
<213> ORGANISM: Homo sapiens

<400> SEQUENCE: 8
aacaaaacac aaaactcttt agagaatc                                       28
```

METHOD FOR MELTING CURVE ANALYSIS OF REPETITIVE PCR PRODUCTS

PRIOR ART BACKGROUND

Hybridization techniques are well known in the art of molecular biology. They allow for the detection of specific sequences, in case a specific hybridization probe is available Usually, the hybridization probe is labeled with a detectable moiety, e. g. a radioactive or fluorescent label.

In addition, Polymerase Chain Reaction (PCR) has become a powerful and wide-spread technology for analysis of nucleic acids. The principles of PCR are disclosed in U.S. Pat. No. 4,683,195 and U.S. Pat. No. 4,683,102 (Mullis et al.). A major improvement in PCR derives from the possibility of measuring the kinetics of a PCR reaction by On-Line detection. This has become possible by means of detecting the amplicon through fluorescence monitoring.

Alternatively, suitable fluorescently labeled hybridization probes which are already present during the amplification reaction may be used subsequently in a homogenous assay without opening the reaction vessel in order to perform a temperature dependent melting curve analysis. For such an analysis the temperature of the sample is increased continiously and the exact melting temperature is determined at which the previosly generated hybrid complex between (amplified) target nucleic acid and hybridization probe is resolved. Such an approach may be used in order to detect differences in melting temperatures of target molecules which only differ from each other by a single nucleotide polymorphism. In other words, melting curve analysis can even be used for the detection or identification of point mutations.

Examples of such techniques are disclosed in detail in WO 97/46707, WO 97/46712 and WO 97/46714 (Wittwer et al.), the disclosures of which are hereby incorporated by reference.

Several detection formats based on target dependent fluorescent signaling have been disclosed, which enable continuous monitoring of the generation of PCR amplification products or identification of mutations during a subsequent melting curve analysis (reviewed in Wittwer et al., Biotechniques, Vol. 22, No, 1, 130–138, 1997). These detection formats include but are not limited to:

a) Increased Fluorescence Resonance Energy Transfer Upon Hybridization

For this detection format, two oligonucleotide hybridization probes each labeled with a fluorescent moiety are used which are capable of hybridizing to adjacent but non overlapping regions of one strand of the amplification product. Preferably, one oligonucleotide is labeled at the 5' end and the second oligonucleotide is labeled at the 3' end. When hybridized to the target DNA, the two fluorescent labels are brought into close contact, such that fluorescence resonance energy transfer between the two fluorescent moieties can take place. As a consequence, the hybridization can be monitored through excitation of the donor moiety and subsequent measurement of fluorescence emission of the second acceptor moiety (WO 97/46714).

In a similar embodiment, only one fluorescently labeled probe is used, which together with one appropriately labeled primer may also serve as a specific FRET pair (Bernard et al., Analytical Biochemistry 235, p. 101–107 (1998)).

b) Molecular beacons

A molecular beacon oligonucleotide is labeled with a fluorescent compound and a quencher compound, which due to the secondary structure of the molecule are in close vicinity to each other. Upon binding to the target DNA, the intramolecular hydrogen bonding is broken, and the fluorescent compound attached at one end of the probe is separated from the quencher compound, which is attached at the opposite end of the probe (Lizardi et al., U.S. Pat. No. 5, 118,801).

However, prior to the time the invention was made, there was no homogenous detection format available which allowed for the quantification of the number of sequence repeats in repetitive sequences. Nevertheless, such an analysis of repeat numbers is of major importance for example in the field of Microsatellite analysis. Microsatellites (MIS) are short tandem repeats which are distributed over the entire human genome. Micro-satellites occur statistically about once every 100,000 base pairs. Up to now 5 classes of MIS have been described which differ from one another in the length of their smallest repetitive unit as a mono-, di-, tri-, tetra- or pentanucleotide repeat. As a rule these repetitive units occur repeatedly 10 to 40 times in a tandem arrangement. Microsatellite instability (MIN) in the form of small deletions or insertions can be detected in many tumour patients if one compares DNA from tumour material with normal DNA of the same individual (Thibodeau et al., (1993), Science, 260, 816–819) (WO 94/19492). This is achieved by amplifying the DNA with the aid of PCR and subsequently separating the amplification products by gel electrophoresis. A permanent replication defect of the tumour cells is regarded to be the cause of MIN (Parsons et al., (1993), Cell, 75, 1227–1236; Shibata et al., (1994) Nat. Genet. 6, 273–281). Such tumours are classified as "replication error-positive" (RER+). An RER+phenotype is characteristic for colorectal tumours in families with HNPCC (hereditary non-polyposis colon cancer) (Aaltonen et al., (1993), Science, 260, 812–816).

The analysis of microsatellites is an extremely attractive method for diagnostic applications as well as for the examination of the tumourigenesis of RER+tumours. Because it is simple to carry out the determination of MIN before sequencing the mismatch repair gene of HNPCC families is a suitable aid in identifying potential RER+patients. MIN analysis is also of major importance for the prognostic diagnosis of sporadic colorectal carcinoma because the occurrence of MIN correlates with a better prognosis (Lothe et al. (1993) Cancer Res., 53, 5849–5852; Thibodeau et al. (1993), Science, 260, 816–819; Bubb et al. (1996) Oncogene, 12, 2641–2649).

MIN can be detected in more than 90% of all HNPCC tumours (Liu et al., (1996) Nature Med., 2, 169–174) whereas MIN only occurs with a frequency of 10–20% in sporadic colorectal tumours (Thibodeau et al. (1993) Science, 260, 816–819; Ionov et al. (1993), Nature, 363, 558–561; Aaltonen et al. (1993) Science, 260, 812–816; Lothe et al. (1993) Cancer Res., 53, 5849–5852). However, MIN is not restricted to colorectal tumours but has also been detected in other tumours. These include among others pancreatic carcinomas (Han et al. (1993) Cancer Res., 53, 5087 –5089), gastric carcinomas (Han et al. (1993) Cancer Res., 53, 5087–5089; Peltomaki et al. (1993) Cancer Res., 53, 5853–5855; Mironov et al. (1994) Cancer Res., 54, 41–44; Rhyu et al. (1994) Oncogene, 9, 29–32; Chong et al. (1994) Cancer Res., 54, 4595–4597), prostate carcinomas (Gao et al. (1994) Oncogene, 9, 2999–3003), carcinomas of the endometrium (Risinger et al. (1993) Cancer Res., 53, 5100–5103; Peltomaki et al. (1993) Cancer Res., 53, 5853–5855) and mammacarcinomas (Patel et al. (1994) Oncogene, 9, 3695–3700).

Prior to the invention, analysis of Microsatellites required in any case a time consuming fragment separation by gel electrophoresis in order to detect the size of the amplification products thereby gaining information about the length of the repeat structure. Thus, there was a need in the art to provide a method for the analysis of the length of repetitive structures without fragment separation. Such a method requires to be quick and easy to perform. In addition, it is advantageous, if such a method can in principle become automated.

BRIEF DESCRIPTION OF THE INVENTION

The new invention relates to a method, wherein the number of repeat sequences which are present in a sample is detemined by means of melting temperature analysis.

Therefore, in a first aspect, the invention relates to a method for analysis of a target nucleic acid consisting of repetitive and non repetitive sequences comprising:
   a) hybridization of at least one polynucleotide hybridzation probe comprising a first segment which is complementary to a non repititive region and a second segment which is complementary to an adjacent repetitive region, said second segment consisting of a defined number of repeats
   b) determination of the melting point temperature of the hybrid which has been formed between the target nucleic acid and the at least one hybridization probe.

According to the invention, the melting point temperature can then be correlated with the number of repeats present in the target nucleic acid Usually, it is advantageous to compare the determined melting temperature value with the melting temperature value obtained for a reference nucleic acid. Therefore, the invention relates also to a method for analysis of a target nucleic acid in a sample said target nucleic acid consisting of repetitive and non repetitive sequences comprising:
   a) hybridization of at least one polynucleotide hybridzation probe comprising a first segment which is complementary to a non repetitive region and a second segment which is complementary to an adjacent repetitive region, said second segment consisting of a defined number of repeats.
   b) hybridization of the same polynucleotide hybridzation probe as in step a) with a target nucleic acid in a reference sample
   c) determination of the melting point temperature of the hybrids which have been formed between the target nucleic acid and the at least one hybridization probe in both the sample and the reference sample
   d) determination of the difference between the two melting point temperatures as a measure for the difference in repeat numbers between the target nucleic acids in the sample and the reference sample.

In order to gain increased sensitivity it has also been proven to be advantageous, if the target nucleic acid is amplified prior to hybridization. Amplification can easily be achieved for example by a Polymerase Chain Reaction.

Usually, the at least one hybridization probe is labeled and the label is preferably a fluorophore. In an even more preferred embodiment, detection according to the FRET/Hybprobe principle is performed. In this case, hybridization is performed with two adjacently hybridizing probes each labeled with a different fluorophor, such that Flourescence Resonance Energy Transfer can take place, when both probes are hybridized to the target nucleic acid.

The new method is applicable for a variety of different experimental set ups, wherein the number of repeat structures in a repetitive sequence needs to be determined.

Consequently, a specific aspect of the invention relates to an application of the new method for the analysis of Microsatellites, and especially Microsatellite Instability (MIN). Such an analysis is well applicable in order to detect hereditary tumors, especially colorectal tumors which are caused by defects in the HNPCC mismatch repair genes.

Similarly, another aspect of the invention focuses on the use of the new method for the identification of an individual in a population, for example in order to resolve forensic problems.

In a further aspect, the invention also relates to respective polynucleotide hybridization probes, comprising a first segment which is complementary to a non repititive region and a second segment which is compementary to an adjacent repetitive region, said second part consisting of a defined number of repeats. In a specific embodiment of the invention, the number of repeats present in the probe is identical to the number of repeats in the wild type of the target sequence. If there is no specific wild type, the number of repeats within the probe is preferably identical to the maximum number of repeats occuring in the repeat locus to be investigated.

Furthermore, it has been proven to be highly advantageous, in case the non repetitive segment of such hybridization probes has a length of 3–10 nucleotides, even more preferably 3, 4, 5 or 6 nucleotides.

In another aspect, the invention relates to a pair of FRET hybridization probes, wherein the first probe consists of non repetitive sequences and the second probe comprises a non repetitive region and a second segment which is complementary to an adjacent repetitive region, said second part consisting of a defined number of repeats. Preferably, in this case the label of the second probe is attached at the non repetitive region of the probe. In a still further aspect, the invention relates to specific polynucleotide hybridization probes having a sequence according to SEQ. ID. NO: 4 for analysis of BAT 26 and SEQ. ID. NO: 7 for analysis of BAT 25, which all are in accordance with the probe characteristics disclosed above.

The following examples, references, sequence listing and figures are provided to aid the understanding of the present invention, the true scope of which is set forth in the appended claims. It is understood that modifications can be made in the procedures set forth without departing from the spirit of the invention.

DETAILED DESCRIPTION OF THE INVENTION

In the context of this invention, the following terms need to be defined further:

A repeat in the context of this invention is a short nucleic acid sequence, which occurs several times in a longer fragment of a DNA or sometimes also in an RNA molecule. Within one repeat, the nucleotide bases are always present in the same order. Those repeats often occur in selfish, non-coding regions of the genome. In most of the cases, these repeat structures are called Microsatellites.

The number of nucleotides generating one repeat may vary. Mononucleotide repeats consist of a single nucleotide base, i.e. A, G, C or T and result in a stretch of Mononucleotides. Dinucleotide repeats consist consist of two types of nucleotide bases, e.g. CA and result in a stretch of alternating sequence, i.e. (CA)n. Triple-, Quadruple—and Pentanucleotide repeats also have been observed frequently. In the context of this invention, an n-nucleotde repeat is understood to be a repetetive structure comprising repeats which have a length n, wherein n is a number between 1, and 10, preferably between 1 and 5 and mostly prefered 1 or two nucleotides.

A repetitive sequence is a sequence with several repeats that are present in a consecutive order or in an inverted order. Sometimes, repetitive sequences may be interrupted by unique, non repetitive sequences. In addition, repetitive sequences have been identified, which contain several types of repeats, especially several types of mononucleotide repeats.

Hybridization probes are polynucleotides having sequences which are completely identical with or exactly complementary to the sequence of the target nucleic acid. Yet, it is also within the scope of the invention, if the probes contain one or several mismatches, as long as they are capable of hybridizing to the analyte under appropriate hybridization conditions. In any case, it has been proven to be particular advantageous, if the sequence identity or complementarity is 100% over a range of at least 10 contiguous residues. It has also been proven to be advantageous, if the length of the probe does not exceed 100 nucleotides, preferably not more than 40 nucleotides However, especially in the context of this invention, hybridization probes may have 5' or 3' overhangs which do not hybridize to the target nucleic acid. This is, because the invention relates to methods for detecting the number of repeats present in the target nucleic acid, and, therefore, the number of repeats in the probe needs to be identical to the maximum number of repeats which can be expected for the target nucleic acid.

Hybridization probes may be conjugated to a detectable entity, for example a fluorescent compound, such that the hybridization event can be detected by methods known in the art.

The term "FRET Hybridization probes" is defined as a pair of hybridization probes, each probe carrying a fluorescent compound, which together may act as a FRET pair thus enabeling the detection of a nucleic acid, when both probes are hybridized adjacently to a target molecule.

The term "Polynucleotide" refers to not only (Desoxy)-Oligo-Ribonucleotides, but also all DNA- or RNA-derivatives known in the art like e.g. Methyl-Phosphonates, Phosphothioates , 2'-O-Alkyl-derivatives as well as Peptide Nucleic Acids, and analogs comprising modified bases like 7-Deaza-Purines.

After hybridization of a hybridization probe with a target nucleic acid, according to the invention, a determination of melting point temperature is performed. The melting point temperature predominantly depends on the size of the double stranded region of the target/probe hybrid. In case a hybridization probe comprising repetitive sequences is used, the hybridization temperature thus depends on and can be correlated with the number of repeats present in the target DNA.

In addition, it is known in the art and should not be neglected, that the melting temperature also depends on
 the GC-content of the double stranded region
 the presence or absence of mismatches within the double stranded region.
 and other factors of minor importances, e.g. the salt concentration of the sample.

The melting point temperature is usually determined experimentally by subjecting the sample to a constitutive increase in temperature and continously measuring the dissociation of the hybridization complex into single strands. The dissociation can be detected by a variety of different methods, for example by a shift in UV absorbance, by surface plamon resonance or preferably by means of flourescence. In the latter case, the hybridization probe is usually labeled with a fluorescent entity, and the generation of a fluorescent signal somehow depends on the formation of the hybridization complex.

In a preferred embodiment, the assay is performed in a homogeneous detection format: For example, the target nucleic acid may be amplified prior to melting temperature determination in a typical PCR reaction with suitable amplification primers. A suitable hybridization probe is already present during the amplification reaction. The hybridization probe preferably carries a fluorescent label which is detectable after appropiate excitation. For example, the hybridization probe may be either a molecular beacon (Lizardi et al., U.S. Pat. No. 5,118,801) or a pair of fluorescently labeled oligonucleotides which together are capable of acting according to the FRET-Hybprobe formate (WO 97/46714). After completion of the PCR-reaction, the temperature of the sample is constitutively increased. Fluorescence can be detected as long as the hybridization probe is bound to the target DNA. However, at melting temperature, the hybridization probe is released from its target, and the fluorescent signal decreases immediately down to the background level. This decrease can be monitored with an appropiate temperature-time plot, such that an exact temperature value can be determined, at which the temperature decrease is observed.

The design of hybridization probes according to the invention requires several preconditions:

First, the probe must comprise a non repetitive hybridizing segment, which is located either at the 5' end or at the 3' end of the probe. The length of the non repetitive segment may vary depending on the special assay conditions. Usually, a segment of at least 3 nucleotides hybridizing with the target sequence has been proven to be sufficient. The presence of such a non repetitive hybridizing sequence has the advantage, that independent from the number of identical repeats in the target sequence, the probe always will exactly hybridize to a defined position on the target nucleic acid, which is the transition between the non repetitive region and the region consisting of repetitive sequences. Second, the number of repeats present in the probe is crucial, to which extend repeats present in the sequence of the target nucleic acid will be detected. More specifically, a hybridization probe containing n repeats used in a method according to the invention will be able to discriminate between several target nucleic acids containing a number between 0 and n repeats. In contrast, the determined melting point temperatures will be equal, for all target nucleic acids which contain n repeats or more than n repeats.

Third, the number of repeats present in a hybridization probe is limited due to the fact that the length of hybridization probes which still can be used for melting point temperature analysis is limited. In this context it has been proven to be advantageous, if the overall length of the hybridisation probe does not exceed 100 nucleotides, preferably does not exceed 80 nucleotides and most preferably does not exceed 60 nucleotides.

Figure 1:
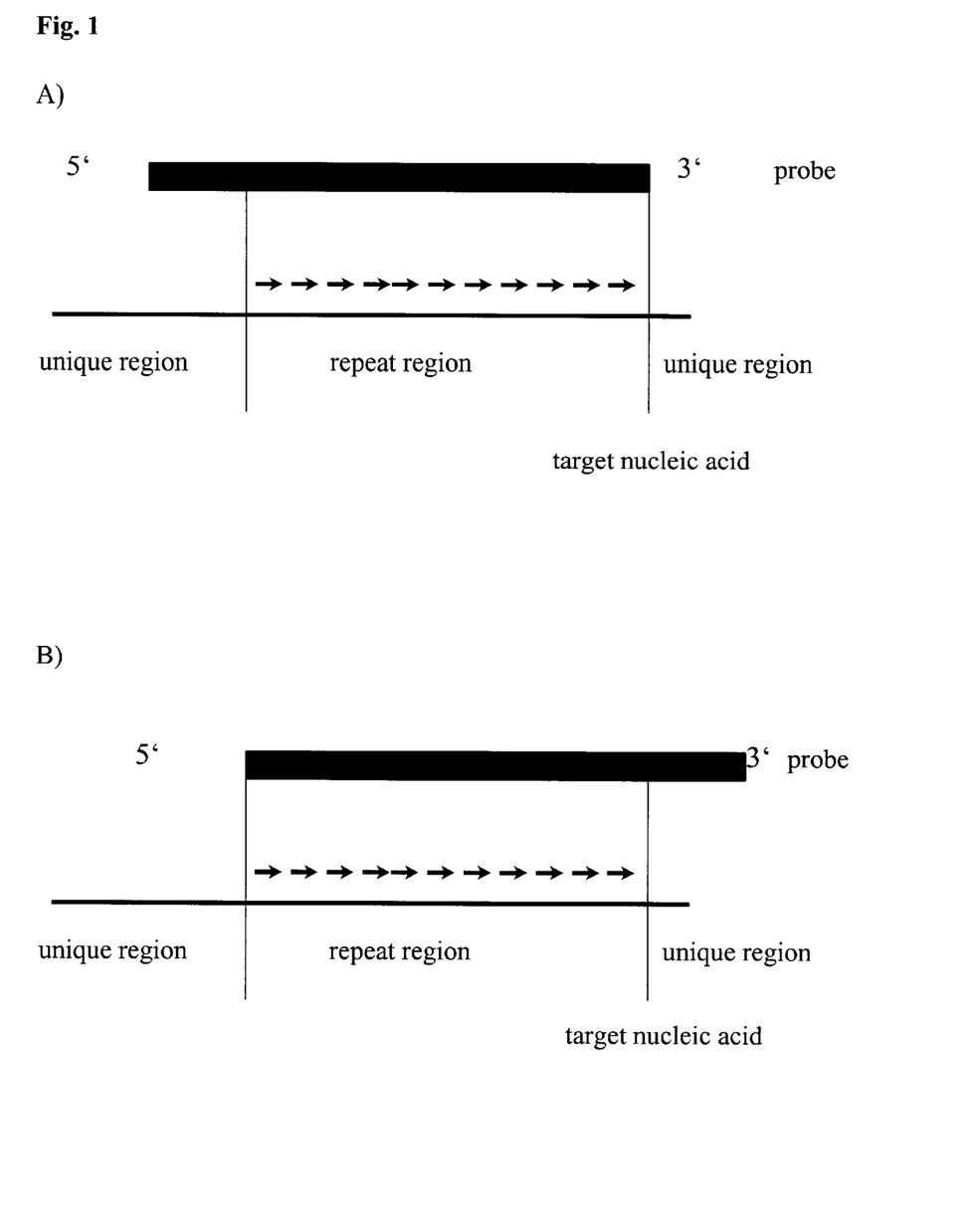
FIG. 1: Schematic drawings of hybridization probes according to the invention. Repeats are indicated as arrows.

FIG. 1 illustrates two alternative probe designs which may be used in case one hybridization probe is applied. This may be the case either in any heterogenous assay format or, alternatively using the homogenous molecular beacon format, wherein a fluorescent entity is bound at or close to either the 5' end or the 3' end of the probe and a quencher moitey is bound at or close to the opposite end of the probe.

In some cases a probe according to the invention may even consist of two non repetitive segments at the 5' and the 3' end connected by an internal repetitive segment.

The probe comprises a non repetitive part which is complementary to one unique region in the target sequence that is located directly adjacent to the repeat region either at its 5' end or at its 3' end. In case of a hybridization event with a target molecule which contains less repeats than the hybridization probe, a single stranded overhang of the probe is generated and the melting temperature is reduced as compared to a situation, wherein the number of repeats in the hybridization probe and the target sequence is equal. More generally, the melting temperature depends directly on the number of repeats present in the target, i.e. the more repeats present in the sample, the higher the melting temperature.

Figure 2:
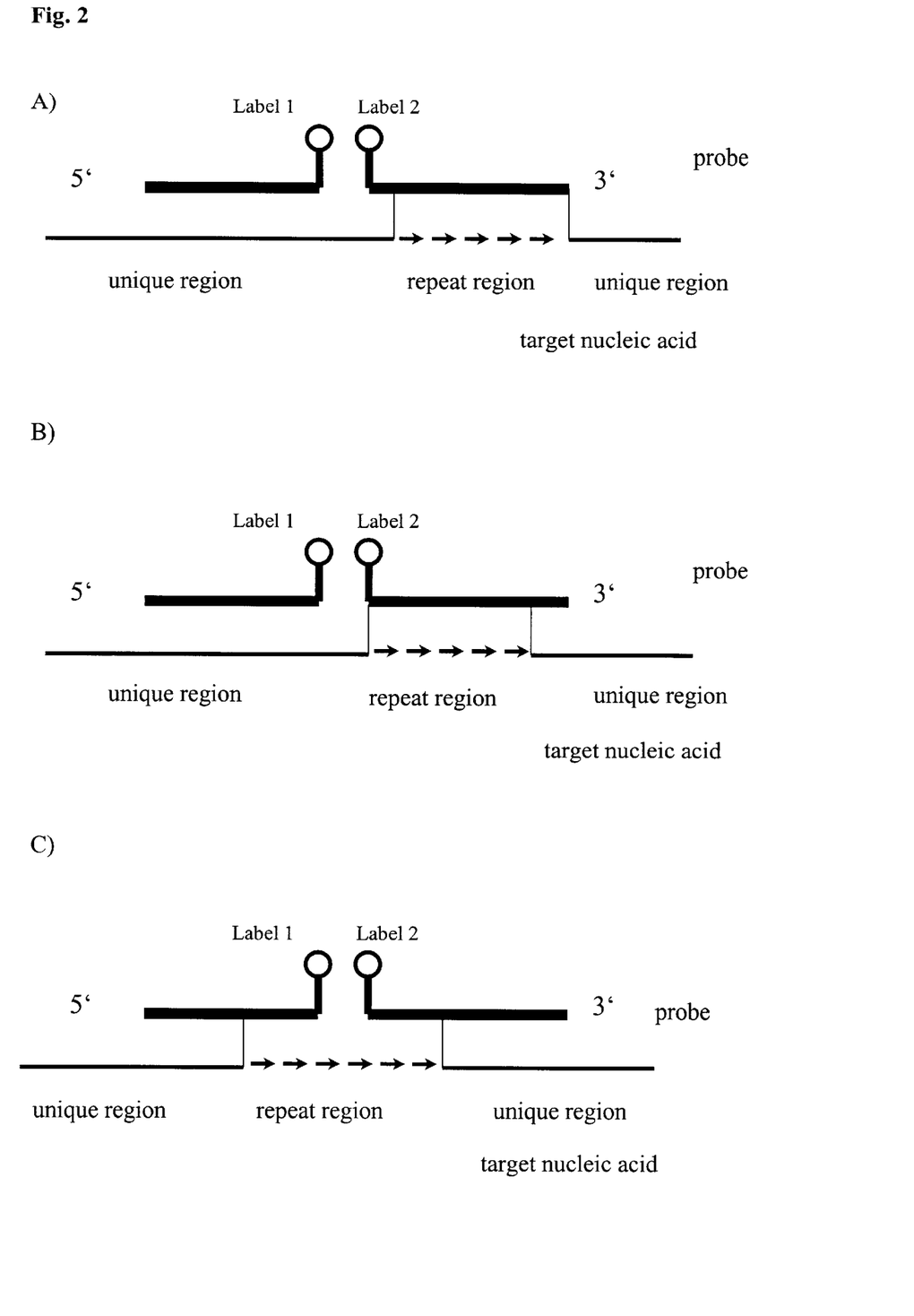
FIG. 2: Schematic drawings of FRET hybridization probes according to the invention. Repeats are indicated as arrows.

FIG. 2 illustrates 3 alternative FRET Hybprobe designs, which however, are not limiting the scope of the invention. For such a probe design, it is necessary that the second probe comprising the repetitive region have a melting temperature which is higher than the melting temperature of the probe containing no repetitive sequences, since the FRET process is interrupted as soon as one probe is dissociated from the target molecule.

FIG. 2A discloses a pair of hybridization probes, wherein the first hybridization probe consists exclusively of non repetitive sequences which are complementary to a region in close vicinity upstream of the repetitive region to be analyzed. The fluorescent label is attached to the 3' end of the probe. The second probe is designed according to the invention and therefore has a sequence complementary to a non repetitive sequence and a second sequence complementary to the repeat sequence of the target nucleic acid. This probe carries the fluorescent label at its 5' end, which is brought into close vicinity with the label of the first probe, when both probes are hybridized to the target molecule.

Alternatively, within the scope of the invention is also an embodiment, wherein the probe consisting exclusively of non repetitive sequences and carries a label at its 5' end and hybridizes downstream of the repetitive region, whereas the second probe designed according to the invention is labeled at its 3' end.

FIG. 2B illustrates an alternative approach of probe design according to the invention. Here, the fluorescent label of the probe containing both repetitive and non repetitive sequences is attached at the repetitive segment of the probe. In case of hybridization with a target molecule which has less repeats than the complementary hybridization probe, loops within this probe will be generated, such that the melting temperature is decreased.

It is also possible to use 2 pairs of hybridization probes, each designed according to the invention. During a melting temperature analysis subsequent to the hybridization event, two significant melting temperatures are observed and the number of repeats present in the target can then be calculated taking both determined melting temperatures into account.

FIG. 2C discloses a still further alternative within the scope of the invention: Both probes comprise a first segment which is complementary to a non repetitive region and a second segment which is complementary to an adjacent repetitive region, said second segment consisting of a defined number of repeats. The two fluorescent labels are then attached within the repetitive region of the two probes. In this particular case, the number of repeats present in both probes together corresponds to the maximum number of repeats which may be expected in the target nucleic acid to be analyzed. Again, if there are less repeats present in the target nucleic acid, loop structures within the hybridization probes are formed and the melting temperatures are lowered.

Since two probes hybridizing to the repeat sequences are used, this embodiment of the invention is especially useful for the analysis of very long repeat structures, moreover because the maximum length of an oligonucleotide hybridization probe is limited by the capacities of conventional oligonucleotide synthesis chemistry. However, such a probe design may result in decreased specificity, since these probes may also bind together to genomic loci different from the repeat locus of interest, in case these loci consist of the same type of repeats.

The invention is suitable for a variety of different applications for analyzing repetitive sequences and especially for analysing Microsatellite repeats: For example, Microstaellite repeat analysis according to the invention can be applied for assessing Loss of Heterozygosity as an indicator for genomic imbalance of tumor suppressor genes, thus beeing indicative of several types of tumors (Knudson, Proc. Natl. Acad. Sci. US 90, p 10914–10921, 1993).

Especially, the new invention is applicable for the analysis of Microsatellite instability, which is indicative for mutations in mismatch repair genes and therefore known to be indicative for hereditary non-polyposis colorectal cancer (HNPCC) (Peltomaki et al., Science 260, p 810–812, 1993). In addition, other types of cancers like e.g. small cell lung cancer also may be prediagnosed.

Finally, the invention is generally applicable for all types of population studies and forensic applications including pesonal identification, tissue typing and population genetic analyses (Koeth et al., J. of Path. 178, p. 239–248, 1996).
The Following Examples Explain the Invention Further:

EXAMPLE 1

Sample Material and Preparation 70 microsatellite stable (MSS) tumors an eight microsatellite instable MSI-H tumors (>=20% instable markers, high MSI) were used for LightCycler microsatellite melting point analysis with mononucleotide repeat loci BAT25 and BAT26. These Markers are described as the most sensitive markers for MSI detection (Hoang et al., 1997, Cancer Res.; Dietmaier et al., 1997, Cancer Res.; Cravo et al., 1999, J Pathol). Tumor and normal tissue regions were microdissected for LightCycler analysis from 5μm sections of formalin-fixed paraffin-embedded tissues by laser assisted (PALM, Bernried, Germany) or manual microdissection. DNA from microdissected tissues was prepared by High Pure PCR Preparation Kit (Roche).

EXAMPLE 2

Real Time PCR of BAT 26

2μl DNA (50–200ng) was mixed with 13μl amplification mix resulting in final concentration of 3mM $MgCl_2$, 0.5 μM BAT26-Upstream (SEQ. ID. NO: 1: TGA CTA CTT TTG ACT TCA GCC) and BAT26-Downstream (SEQ. ID. NO: 2: AAC CAT TCA ACA TTT TTA ACC) amplification primers, 0.15 µM BAT26-Donor-Hybridization probe (SEQ: ID. NO: 3: GCA GCA GTC AGA GCC CTT AAC CT) which was labeled with Fluorescein at ist 3' end, 0,15 µM BAT26-Acceptor-Hybridization probe (SEQ. ID. NO: 4: TCA GGT AAA AAA AAA AAA AAA AAA AAA AAA AA) which was labeled at ist 5' end with LightCycler fluorescent dye LC-Red-640 (Roche Molecular Biochemicals), and 1x LightCycler™ DNA Master Hybridization Probes-Mix (Roche Molecular Biochemicals).

Figure 3:
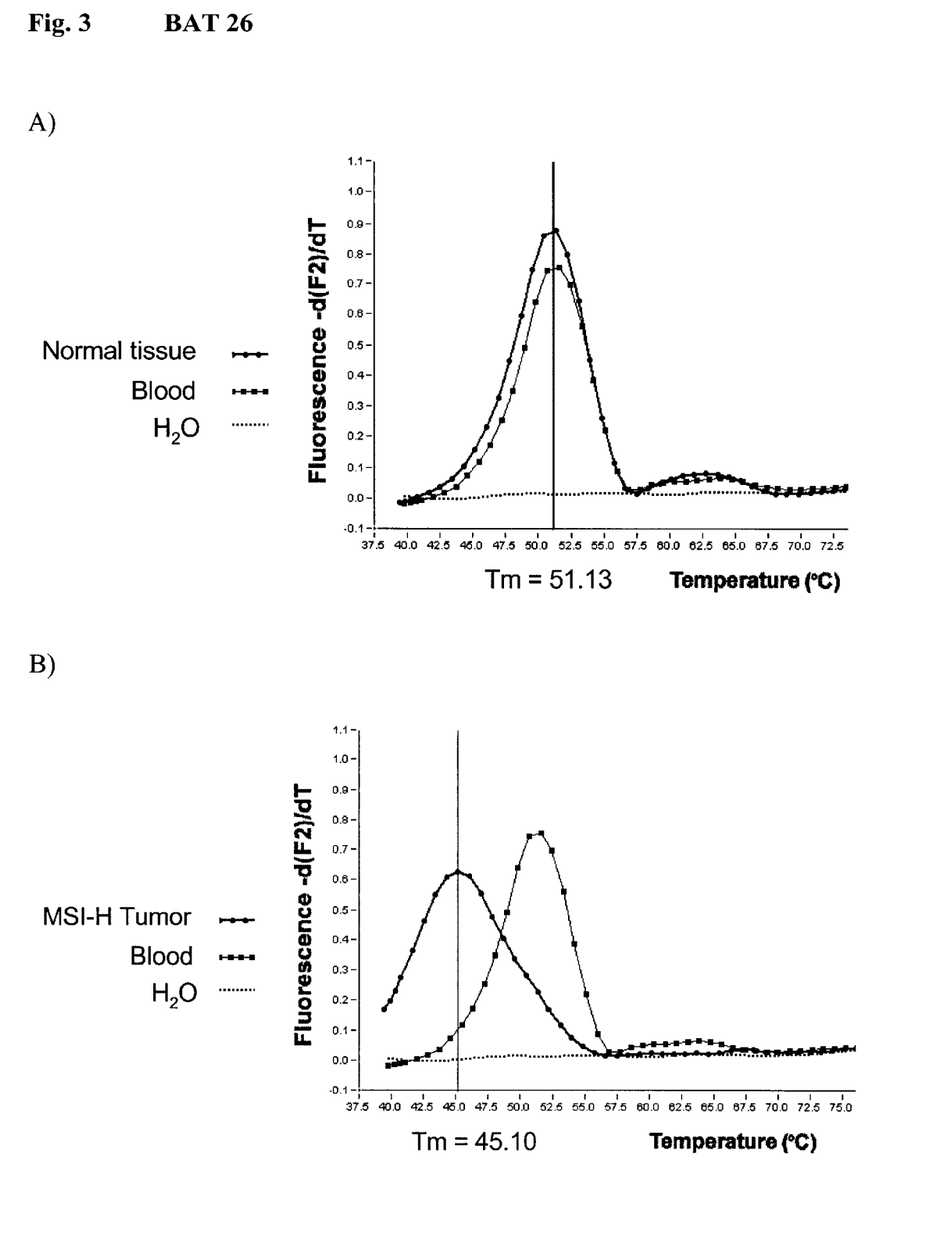
FIG. 3: Microsatellite Analysis of Mononucleotide repeat locus BAT 26 according to the invention

The LightCycler (Roche Molecular Biochemicals) was used for subsequent Real Time PCR amplification monitoring. BAT26 PCR amplification program started with a single denaturation step at 95° C. for 90 sec and proceded with 50 cycles of 95° C./0 sec, 60° C./10sec, 50° C./3 sec for signal detection, and 72° C./ 10 sec. Afterwards, a melting profile was established by incubating the amplicons at 95° C/0sec, 35° C./30sec, and increasing temperature to 95° C. with 0.2°/sec with a continously canal F2 detection Amplification and detection of BAT26 by real time PCR and melting point analysis was possible in 125/153 (82%) and 26/31 (83%) formalin-fixed and paraffin embedded tissue samples, respectively. BAT26 melting point analysis revealed a melting temperature (Tm) of 51–51,8° C. for normal tissue, blood or MSS tumors (FIG. 3A). In contrast, each of 7 MSI-H tumors with defective hMSH2 or hMLH1 protein expression and a 100% MSI rate showed an altered Tm which ranges from 43–46° C. (FIG. 3B).

EXAMPLE 3

Real Time PCR of BAT 25

Except otherwise indicated, amplification and melting curve analysis was performed as in example 2.

0.5 µM BAT25-Upstream (SEQ. ID. NO: 5: TCG CCT CCA AGA ATG TAA GT) and BAT25-Downstream (SEQ.ID. NO: 6: TCT GCA TTT TAA CTA TGG CTC) primers as well as 0.15 µM BAT25-Donor-Hybridization probe (SEQ. ID. NO: 7: CAA AAA AAA AAA AAA AAA AAA AAA AAT CA) which was labeled with Fluorescein at its 3' end and 0,15 µM BAT25-Acceptor-Hybbridization probe (SEQ. ID. NO: 8: AAC AAA ACA CAA AAC TCT TTA GAG AATC) which was labeled at its 5' end with LightCycler fluorescent dye LC-Red-705 (Roche Molecular Biochemicals) were used for BAT25 LightCycler amplification.

Figure 4:
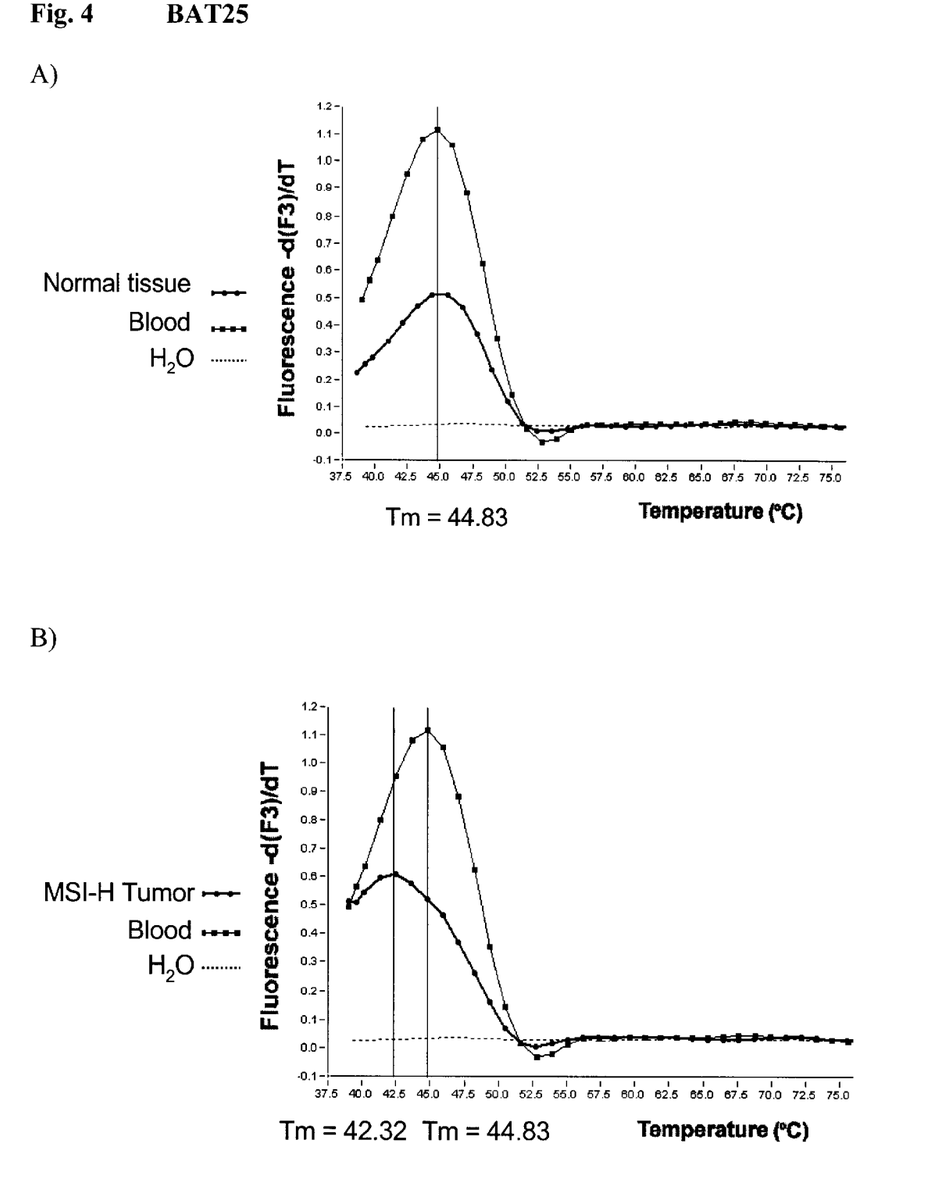
FIG. 4: Microsatellite Analysis of Mononucleotide repeat locus BAT 25 according to the invention

The BAT25 amplification program contained a single denaturation step at 95° C. for 90 sec and 50 cycles of 95° C./0 sec, 60° C./10sec for signal detection, and 72° C./10sec. Meltin profile was established by incubating the amplicons at 95° C./0sec, 30° C./30sec and a temperature ramp to 95° C. with 0.2°/sec with a continously F3 detection. Results are shown in FIG. 4. The melting point analysis of BAT25 revealed a Tm of 44.5° C. in normal tissue and MSS tumor DNA (FIG. 4A) whereas BAT25-Tm of two MSI-H tumors was significantly lower at 42° C. (FIG. 4B).

EXAMPLE 4

Real Time Duplex PCR of BAT 216 and BAT 25

For Duplex-PCR in order to analyze BAT 25 and BAT 26 within one tube, primers and FRET-Hybridization probes for both BAT25- and BAT26 according to SEQ. ID. No: 1–8 were combined in concentrations given in examples 2 and 3.

The LightCycler amplification program was as follows: a single denaturation step at 95° C. for 90sec and 50 cycles of 95° C./0 sec, 60° C./10sec, 45° C./2sec. for signal detection 72° C./10sec. The duplex melting curve program was: 95° C./0 sec, 30° C./30 sec and a temperature ramp to 95° C. with 0.2°/sec with a continously fluorescence detection at F2and F3.

Figure 5:
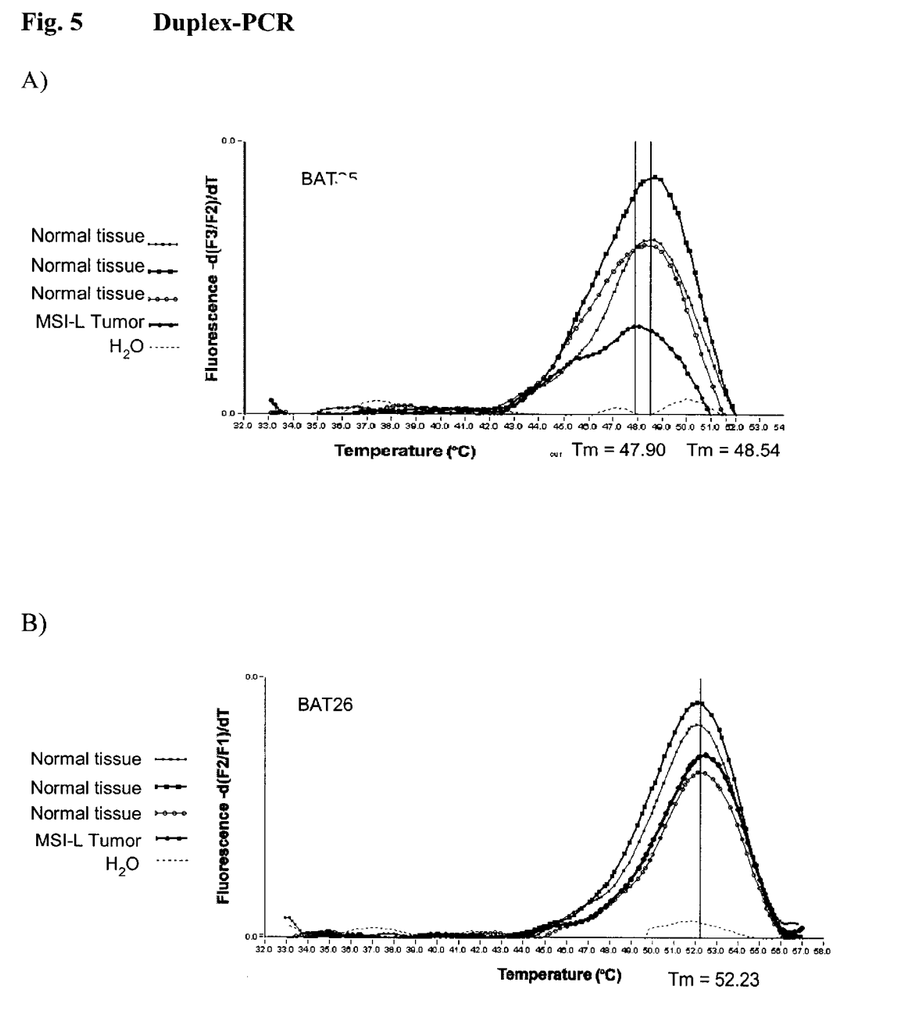
FIG. 5: Multiplex Microsatellite Analysis of Mononucleotide repeat loci BAT 25 and BAT 26 according to the invention

When duplex LightCycler amplification of BAT25 and BAT26 was done, higher Tm values were obtained as compared to seaparate LightCycler analyses for BAT 25 and 26 (FIG. 5). For BAT25 the difference in Tm was four degrees (FIG. 5a). The Tm values of BAT26 were one degree higher (FIG. 5b)

List of References

Aaltonen et al., (1993), Science, 260, 812–816
Bernard et al., Analytical Biochemistry 235, p. 101–107 (1998)
Bubb et al. (1996) Oncogene, 12, 2641–2649
Chong et al. (1994) Cancer Res., 54, 4595–4597
Cravo et al., 1999, J Pathol
Dietmaier et al., 1997, Cancer Res.
Gao et al. (1994) Oncogene, 9, 2999–3003
Han et al. (1993) Cancer Res., 53, 5087–5089
Hoang et al., 1997, Cancer Res.
Ionov et al. (1993), Nature, 363, 558–561
Knudson, Proc. Natl. Acad. Sci. US 90, p 10914–10921, 1993
Koeth et al., J. of Path. 178, p. 239–248, 1996
Liu et al., (1996) Nature Med., 2, 169–174
Lizardi et al., US 5, 118,801
Lothe et al. (1993) Cancer Res., 53, 5849–5852
Mironov et al. (1994) Cancer Res., 54, 41–44
Parsons et al., (1993), Cell, 75, 1227–1236
Patel et al. (1994) Oncogene, 9, 3695–3700
Peltomaki et al. (1993) Cancer Res., 53, 5853–5855
Peltomaki et al., Science 260, p 810–812, 1993
Rhyu et al. (1994) Oncogene, 9, 29–32
Risinger et al. (1993) Cancer Res., 53, 5100–5103
Shibata et al., (1994) Nat. Genet. 6, 273–281
Thibodeau et al. (1993) Science, 260, 816–819
Wittwer et al., Biotechniques, Vol. 22, No, 1, 130–138, 1997

I claim:

1. A method for analysis of a target nucleic acid consisting of repetitive and non repetitive sequences comprising:
   a) hybridizing the target nucleic acid with at least one polynucleotide hybridization probe comprising a first segment which is complementary to a non repetitive region and a second segment which is complementary to an adjacent repetitive region, said second segment consisting of a defined number of repeats; and
   b) determining the melting point temperature of the hybrid which has been formed between the target nucleic acid and the at least one hybridization probe, wherein the melting point temperature is correlated with the number of repeats present in the target nucleic acid.

2. A method for analysis of a target nucleic acid in a sample said target nucleic acid consisting of repetitive and non repetitive sequences comprising:
   a) hybridizing the target nucleic acid in the sample with at least one polynucleotide hybridzation probe comprising a first segment which is complementary to a non repetitive region and a second segment which is compementary to an adjacent repetitive region, said second segment consisting of a defined number of repeats;
   b) hybridizing the same polynucleotide hybridization probe as in step a) with a target nucleic acid in a reference sample;
   c) determining the melting point temperature of the hybrids which have been formed between the target nucleic acid and the at least one hybridization probe in both the sample and the reference sample; and
   d) determining the difference between the two melting point temperatures as a measure for the difference in repeat numbers between the target nucleic acids in the sample and the reference samples.

3. The method according to claim 1 or 2, wherein the target nucleic acid is amplified prior to hybridization.

4. The method according to claim 3, wherein the at least one hybridization probe is labeled.

5. The method according to claim 4, wherein hybridization is performed with two adjacently hybridizing probes each labeled with a different fluorophore, such that Flourescence Resonance Energy Transfer can take place, when both probes are hybridized to the target nucleic acid.

6. The method according to claim 5, wherein the flurophore of the probe comprising a first segment which is complementary to a nonrepetitive region and a second segment which is complementary to an adjacent repetitive region is attached at the first segment of the probe.

7. The method according to claim 4, wherein the hybridization probe is labeled with a flurophore.

* * * * *